(12) United States Patent
Gavriely

(10) Patent No.: US 8,147,417 B2
(45) Date of Patent: Apr. 3, 2012

(54) TOURNIQUET TIMER

(75) Inventor: Noam Gavriely, Haifa (IL)

(73) Assignee: OHK Medical Devices Ltd., Haifa (IL)

( * ) Notice: Subject to any disclaimer, the term of this patent is extended or adjusted under 35 U.S.C. 154(b) by 178 days.

(21) Appl. No.: 12/010,297

(22) Filed: Jan. 23, 2008

(65) Prior Publication Data
US 2008/0177159 A1    Jul. 24, 2008

Related U.S. Application Data

(60) Provisional application No. 60/881,703, filed on Jan. 23, 2007.

(51) Int. Cl.
A61B 17/00 (2006.01)

(52) U.S. Cl. ........................................ 600/499; 606/203

(58) Field of Classification Search .................. 600/481, 600/483–485, 490–503; 606/201–203
See application file for complete search history.

(56) References Cited

U.S. PATENT DOCUMENTS

| 4,077,402 | A | * | 3/1978 | Benjamin et al. | 601/150 |
| 4,297,996 | A | * | 11/1981 | Uriza | 606/203 |
| 5,485,848 | A | * | 1/1996 | Jackson et al. | 600/485 |
| 6,149,666 | A | * | 11/2000 | Marsden | 606/203 |

* cited by examiner

Primary Examiner — Charles A Marmor, II
Assistant Examiner — Carrie R Dorna
(74) Attorney, Agent, or Firm — Graeser Associates International Inc; Dvorah Graeser

(57) ABSTRACT

A timer for tourniquet, adapted for application in a surgery, emergency or military situations to stop arterial blood loss in an injured limb, which is optionally activated by use of the tourniquet and/or optionally provided in association with a monitor for a plurality of tourniquets.

26 Claims, 9 Drawing Sheets

TOURNIQUET TIMER

RELATED APPLICATION

The present application claims the benefit under 119(e) of U.S. Provisional Patent Application No. 60/881,703 filed on Jan. 23, 2007, the disclosure of which is incorporated herein by reference.

FIELD AND BACKGROUND OF THE INVENTION

The present invention, in some embodiments thereof, relates to medical techniques. More particularly, but not exclusively, the present invention relates to the devices and methods for use in surgery and in emergency and military medicine.

Arterial tourniquets have been used in surgery, emergency and military medicine for over 300 years for an emergency treatment of shock caused primarily by loss of blood through internal bleeding or injury of the human body (see U.S. Pat. Nos. 34,112; 35,038). The term shock, used for more than 150 years, was defined to characterize the alarming symptoms known as a result of a wide variety of causes, both physical and psychological. One of the most frequently encountered types of shock is the traumatic one, caused after a severe injury. As a result of the injury, a disturbance of fluid balance occurs which is manifested by a decreased volume of blood and tissue perfusion.

It is generally accepted that the application of an arterial tourniquet to a limb to prevent bleeding or establish a bloodless surgical field must be limited in time irreversible damage to the limb is to be prevented.

U.S. Pat. No. 4,294,261 "Logic-controlled occlusive cuff system" describes a system that comprises a pressure cuff and a source of regulated compressed gas feeding the cuff through an electrically-operated fill valve. In response to an external start signal, a logic network starts the pressurization cycle and a timer. A pressure transducer continuously monitors the pressure in the cuff. The timer, after a selected time delay, opens the vent valve to the ambient pressure, thereby ending the pressurization cycle.

U.S. Pat. No. 4,321,929 "Tourniquet" disclosed an automatic tourniquet which has a control system therefore. An electronic sensing means senses physiological variables and generates signals which are applied to the computer or microprocessor, which analyzes such signals and generates control signals for controlling the motors operating pumps. A tourniquet has a timer is connected for controlling same and providing intervals of time during which blood pressure is sensed and the tourniquet is tightened.

U.S. Pat. No. 6,746,470 and US 2003/0139766 "Emergency and Military Tourniquet for Pre-Hospital Use" disclose a pneumatic tourniquet adapted for self application by an injured person in a military or emergency situation to stop blood loss from an injured limb. A tourniquet comprises a bladder cuff with a clamp means for securing the bladder around the limb and an indicator module connected to the bladder. The indicator module is indicates cuff pressure and elapsed inflation time interval up to 2 hours and is supplied with a microprocessor and an alarm indicator that provides an audible and visual indication of alarm to the crew or user. The microprocessor is programmed to determine elapsed inflation time by measuring the duration of time that the pressure has exceeded a predetermined pressure threshold. The alarm indicator may also be activated by microprocessor if unusually high pressures are detected in the bladder (for example pressures greater than 400 mmHg).

U.S. Pat. No. 6,149,666 disclosed a tourniquet includes an elongate flexible body having an electronic lead and a pair of spaced-apart connection location for attachment to secure the body in circumscribing relationship about the limb. The tourniquet is provided also with a microchip and a timer for generation of an alarm signal upon passage of an elapsed time. The microchip and timer may be modified to include a wide variety of audio signals at various desirable periods of time.

SUMMARY OF THE INVENTION

According to an aspect of some embodiments of the present invention there is provided a method of using a tourniquet with a timer that generates two or more warnings, for example, both an advance warning that a usage time is about to expire and a final warning when a usage time expires and a danger time begins. Optionally, a further warning is generated when a further increase in danger is created by continued tourniquet use. In an exemplary embodiment of the invention, the advance warning is selected to match a procedure using the tourniquet, to provide sufficient time to complete the procedure and/or sufficient time to temporarily perfuse a limb to which blood flow is blocked.

In an exemplary embodiment of the invention, the method comprising attaching around a tourniquet a limb so as to block blood flow therein, at least estimating a start time for the attaching and generating a first and a second warning. The first warning is optionally generated before a danger time is reached and/or based on information and/or estimation about worsening of the patient's condition with respect to the limb. The second warning is generated when a danger time is reached, based on the estimated start time. Optionally, the danger time is specifically determined for a procedure, for example, based on patient age. Optionally, the danger time duration is estimated automatically.

Optionally, a start time may be automatically estimated when the tourniquet is activated. Optionally, the application of the tourniquet to a limb is detected automatically.

Optionally, a user's input of the time when the tourniquet is activated is used for estimating a starting time and duration.

In an exemplary embodiment of the invention, the generating of a first warning, before a danger time is reached, is realized in the time period from the moment of tourniquet's activation up to a danger time marked on a timer. This warning is optionally based on preloaded or after provided patient's information, including data such as patient's age, instantaneous blood flow, blood pressure and/or oxygenation level. In an exemplary embodiment of the invention, a separate sensor (e.g., blood flow sensor, oxygenation) is used for measuring this information and may be integrated with the tourniquet, for example, downflow of the tourniquet or provided connect by wired or wireless means to the tourniquet.

In an exemplary embodiment of the invention, the generating of the first warning before a danger time is reached, sets in motion the opening and then re-closing of the tourniquet in response to warning and/or data preloaded in the timer or a control system. Optionally or alternatively, the generating of the second warning when a danger time is reached sets in motion the tourniquet's deactivation. The generating of the first and/or the second warning are accompanied by sound and/or light signals, and/or a wireless transmitted warning. Optionally, recorded speech, read out or displayed texts, optionally including detailed warning with instructions for a user are used as warning signals. A warning may be provided in multiple locations, such as on the tourniquet and/or on a control system.

The detailed warning may be transmitted wirelessly to a central computer with one display for performing the data from several tourniquets. The method may be realized, for example in case of emergency usage, using several tourniquets that are controlled by one timer system coupled to a central computer.

According to an aspect of an exemplary embodiment of the present invention there is provided a tourniquet, comprising a pressure applying means and a timer means. The pressure applying means is adapted to be mounted on a limb so as to block arterial flow therein. The timer means is adapted to be mounted on the pressure applying means or coupled with this pressure applying means to at least estimate and/or note a start time of the application, to monitor a duration of this application and/or a patient's condition, to generate a first warning before a danger time is reached, based on the information about the worsening of the patient's condition and to generate a second warning when a danger time is reached, based on the estimated start time.

According to some embodiments of the invention, the pressure applying means is supplied with a pressure-sensitive means (PSM) and a transmitter which transmits a signal responsive to at least one of the activation of the timer means and activation of the pressure applying means.

According to some of the embodiments of the invention, the pressure applying means and the pressure-sensing means (PSM) are provided as a unit which is equipped with an independent energy source.

According to some embodiments of the invention, the pressure-sensitive means (PSM) is a mechanically activated trigger (MAT) which is activated by the usage of the pressure applying means and contains a mechanical stretching sensor, a tensile force sensor or a deformation bending sensor. Every of these sensors may be made as an elastic or a spring-loaded micro-switch embedded within the stretchable matrix of the tourniquet. Optionally or alternatively, the PSM is chemically activated trigger in which mechanical activation and/or environment cause a chemical timer to optionally operate in a manner which can be sensed and used to generate a time-up signal.

According to an aspect of some embodiments of the present invention there is provided a tourniquet system with wireless central control and/or monitoring for one or more tourniquets. The tourniquet system comprising at least one tourniquet with a pressure applying means and a transmitter coupled with this means. The transmitter sends a signal associated with activation of the pressure applying means. The tourniquet system comprising also a remote controller with a transceiver and circuitry display to generate a signal detectable by a user, regarding to the status of the tourniquet that sent a signal, based on the signal, associated with activation of the pressure applying means. Optionally, the control is remote from the tourniquets. Alternatively, the control is local, for example, being within 10-50 meters distant The signal is optionally displayed on a circuitry display and may include one or more of: a tourniquet's ID-number, a patient's data, the time of tourniquet application, the time of activation of pressure applying means, the time of generating of the first and the second warning before and when a danger time is reached and/or the time (e.g., like other times, absolute or relative) of the user's input to the system. This signal may include the status of at least one tourniquet, for example, if it is applied or not.

A signal detectable by a user is optionally displayed on a circuitry display when at least one tourniquet sends by its transmitter a signal associated with activation of pressure applying means. This signal detectable by a user is optionally changed on the circuitry display, when at least one tourniquet sends by its transmitter the signals associated with generating the first and/or the second warning signals.

According to some embodiments of the invention, the remote controller is a computer with a circuitry display and supplied with a transceiver (or at least a receiver) and at least one timer means for monitoring at least one tourniquet from multiple tourniquets connected with a remote station where this computer is mounted. IN some embodiments, the timer is on the tourniquet(s).

According to some embodiments of the invention, the remote station with the computer, transceiver and at least one timer means for monitoring the multiple tourniquets, may be made in stationary design for the hospital use or in portable design to be used in military and emergency situations.

According to some embodiments of the invention, the remote station with the computer, transceiver and at least one timer means, is integrated with a mobile patient monitor or within an anesthesia monitoring system, optionally with the possibility of communication to a pre-set cellular phone number (or other communication means).

According to some embodiments of the invention, the remote station with the computer, transceiver and at least one timer means, has a feedback connections with one or more of the multiple tourniquets for control thereof, for example, one or more of initializing the stop or release operations of the tourniquets, their opening and then re-closing or complete deactivation.

According to an aspect of some embodiments of the invention, there is provided a tourniquet, comprising a pressure applying means and a timer means, optionally a chemical timer means. The pressure applying means is adapted to be mounted on a limb so as to block arterial flow therein. The chemical timer means is optionally adapted to be mounted on the pressure applying means or coupled with this pressure applying means to at least estimate and/or note a start time of the application, to monitor a duration of this application and a patient's condition, to generate a first warning before a danger time is reached, based on the information about the worsening of the patient's condition and to generate a second warning when a danger time is reached, based on the estimated start time.

According to some embodiments of the invention, the chemical timer means comprises at least one strip made of a material chosen from a group, including the liquid crystals, chemical compounds, leuco dyes, thermochromics and/or photochromics.

According to some embodiments of the invention, the chemical timer means is made as at least one strip of material which at least once changes its color under affect of one or more agent chosen from a group, including the light, air, temperature, tension, chemical activators.

According to some embodiments of the invention, the chemical timer is activated by the user's input (e.g., breaking of a vial) which at least estimates a start time for the attached tourniquet, makes the note of time when tourniquet is activated and estimates the application duration of the tourniquet to a limb.

According to some embodiments of the invention, the chemical timer is activated by manual input of the user who turns therefore at least one handle and/or tears off this at least one strip cover sheet.

According to some embodiments of the invention, at least one strip of the chemical timer generates a first warning before a danger time is reached, based on the information about the worsening of the patient's condition, whereas other strip of this chemical timer generates a second warning when a danger time is reached, based on the estimated start time.

According to other embodiments of the invention, the same strip of the chemical timer generates a first warning before a danger time is reached, based on the information about the worsening of the patient's condition and a second warning when a danger time is reached, based on the estimated start time.

In some embodiments of the invention, the chemical means is used to detect the start of tourniquet use and/or to mark out time. Optionally, changes are detected manually or by a suitable sensor and used to generate a warning. Optionally, the change comprises a color change visible to a human user.

According to all embodiments of the invention, the tourniquet's timer is adapted for sterilization by one of the methods from the group, including: gas, steam, ultraviolet or radiation sterilization.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to medical techniques. More particularly, but not exclusively, the present invention relates to the devices and methods for use in surgery and in emergency and military medicine.

Figure 1:
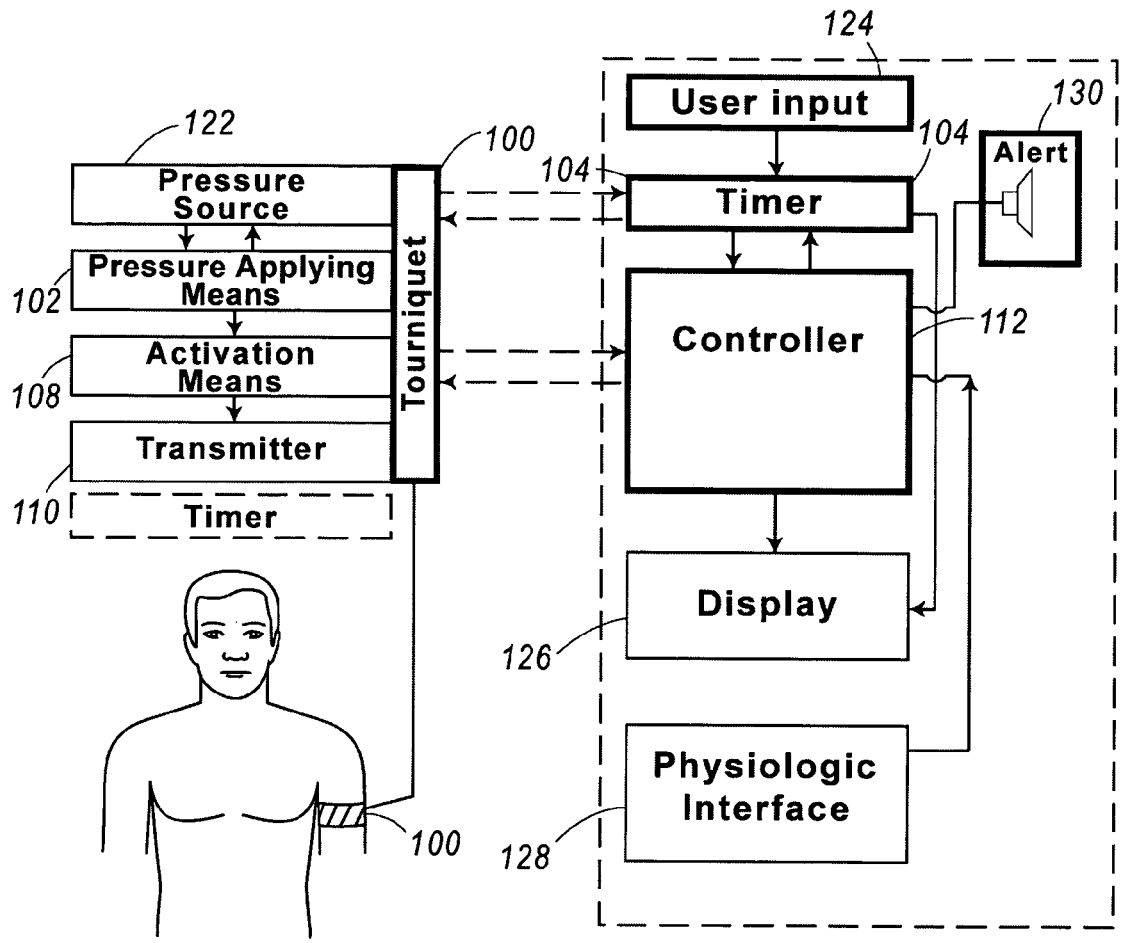
FIG. 1 shows a schematic concept skeleton of tourniquet timer with various optional device components, in accordance with exemplary embodiments of the invention.
Figure 5:
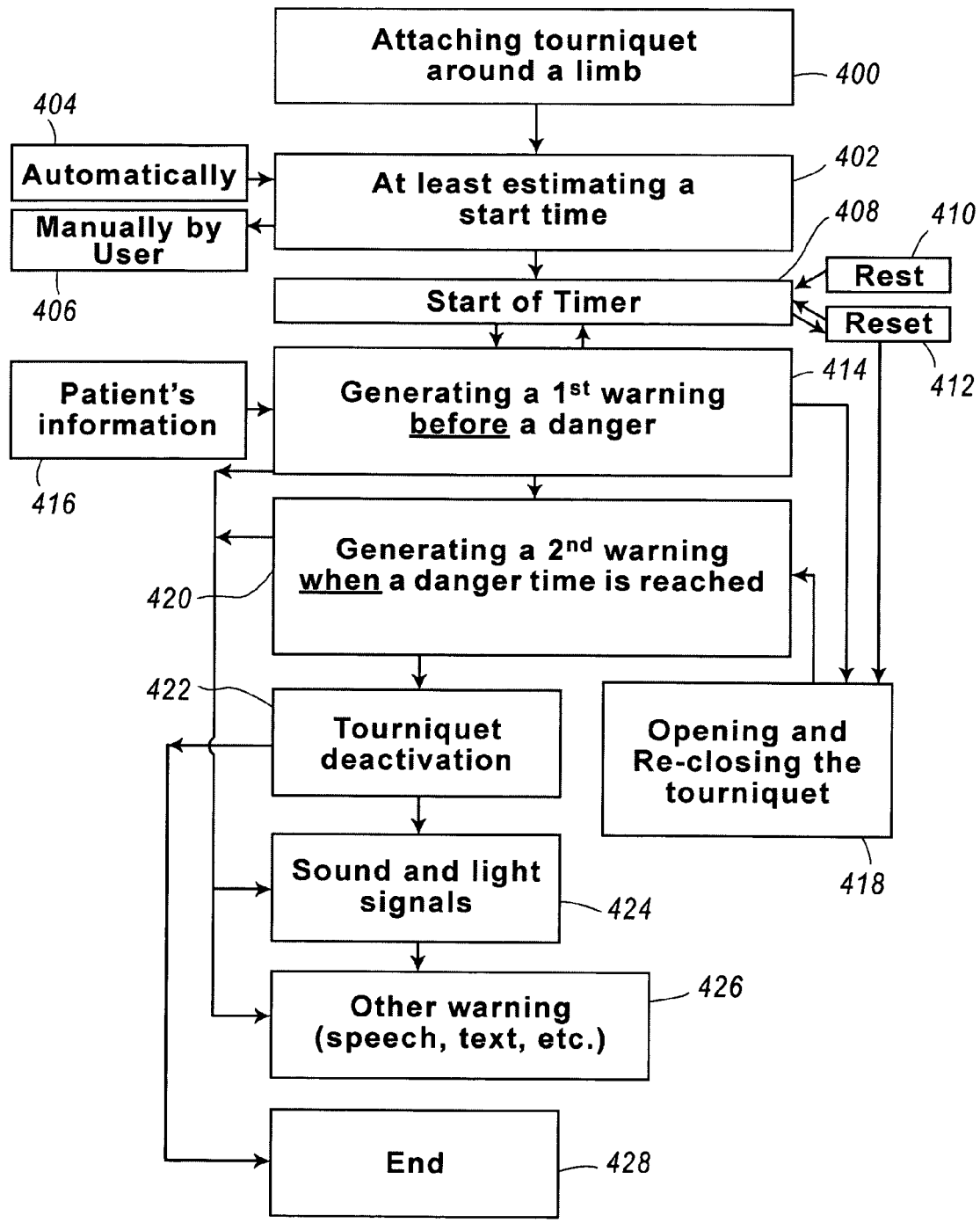
FIG. 5 shows a flowchart of using a tourniquet for treatment according to an exemplary embodiment of the present invention.
Figure 6:
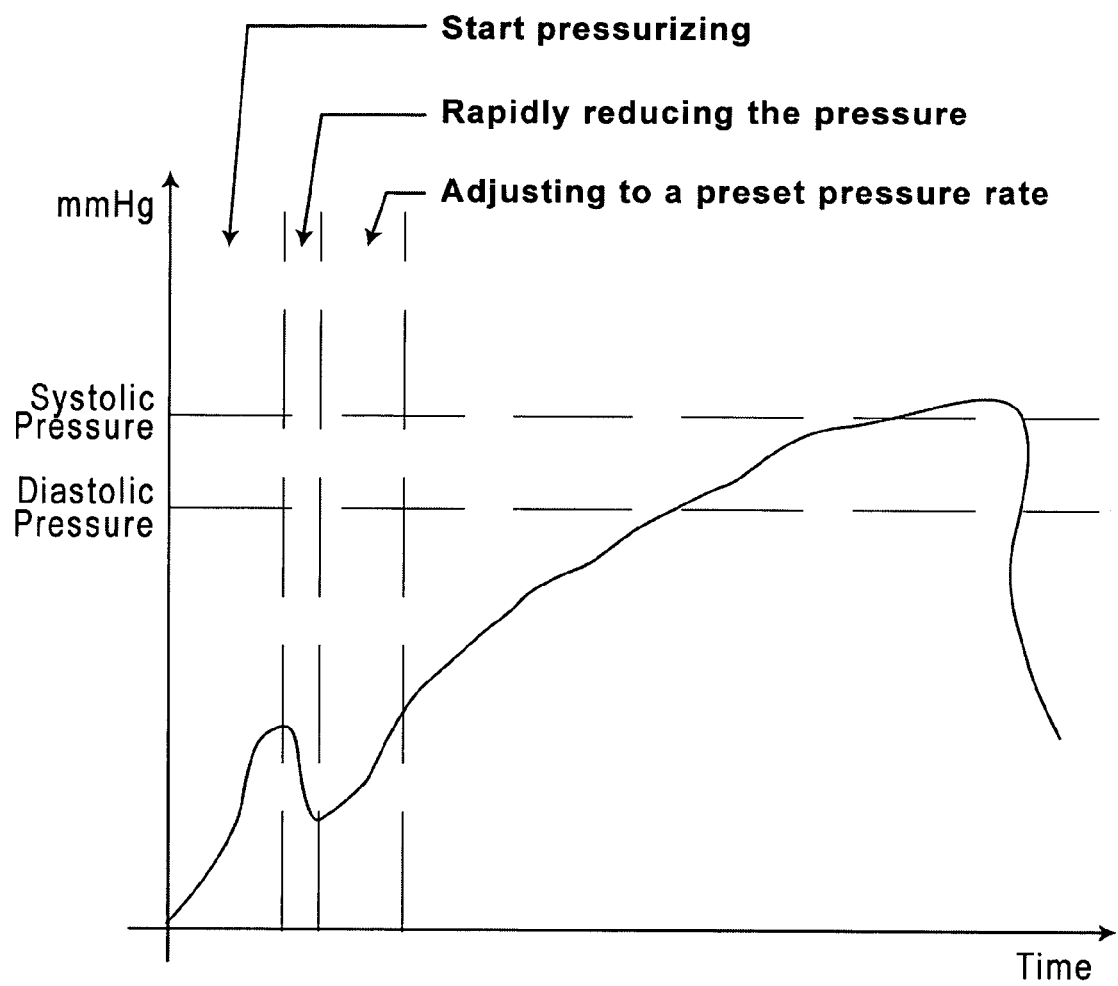
FIG. 6 shows a scheme of tourniquet control.
Figure 7:
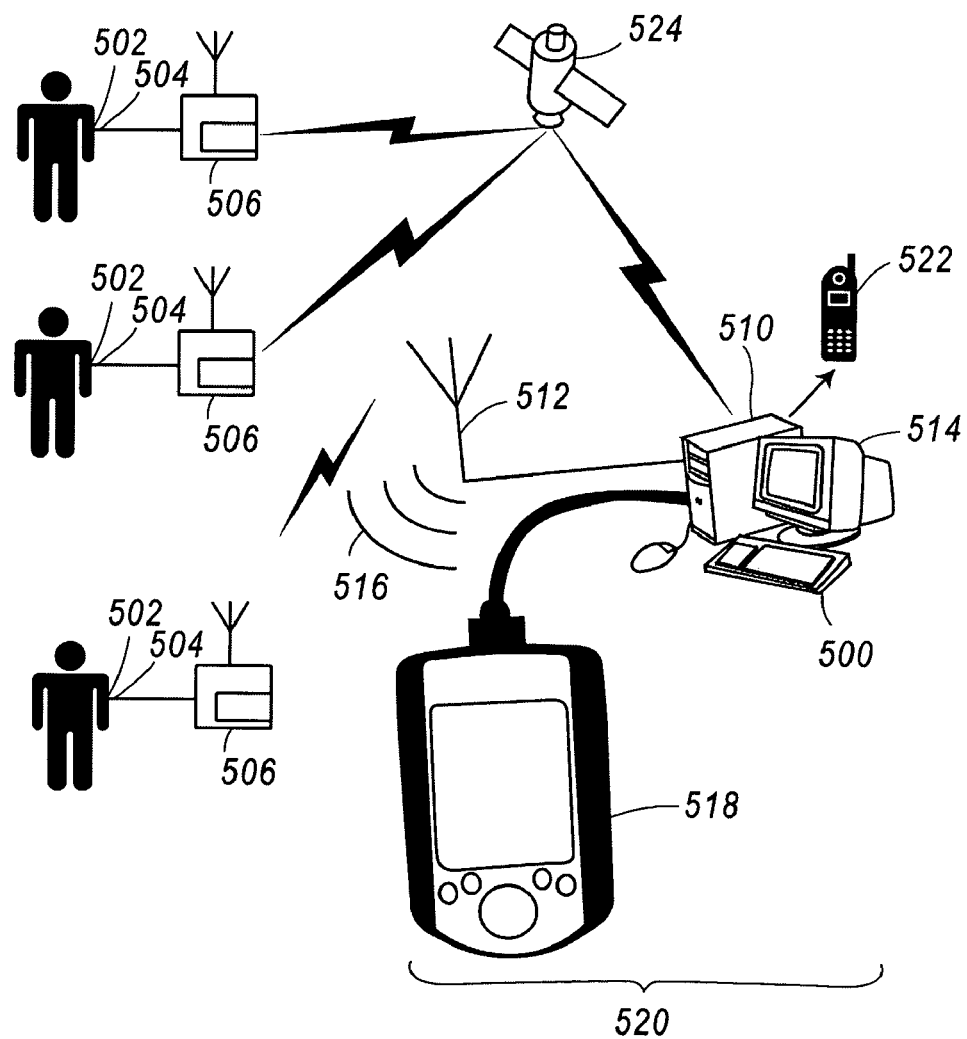
FIG. 7 shows a scheme of a tourniquet system with wireless central control for one or more tourniquets, in accordance with an exemplary embodiment of the invention.
Figure 8B:
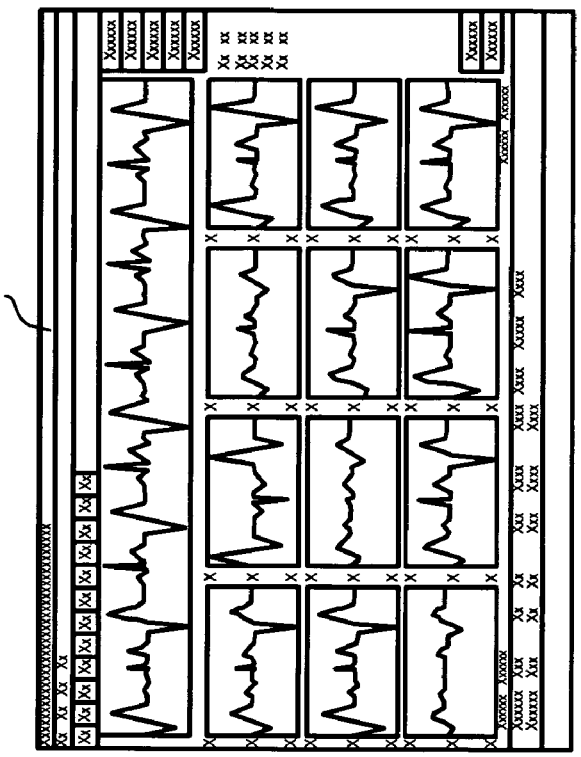
FIGS. 8a and 8b show a circuitry display which displayed signals detectable by a user and regarding the tourniquets that sent these signals, in accordance with an exemplary embodiment of the invention.
Figure 8A:
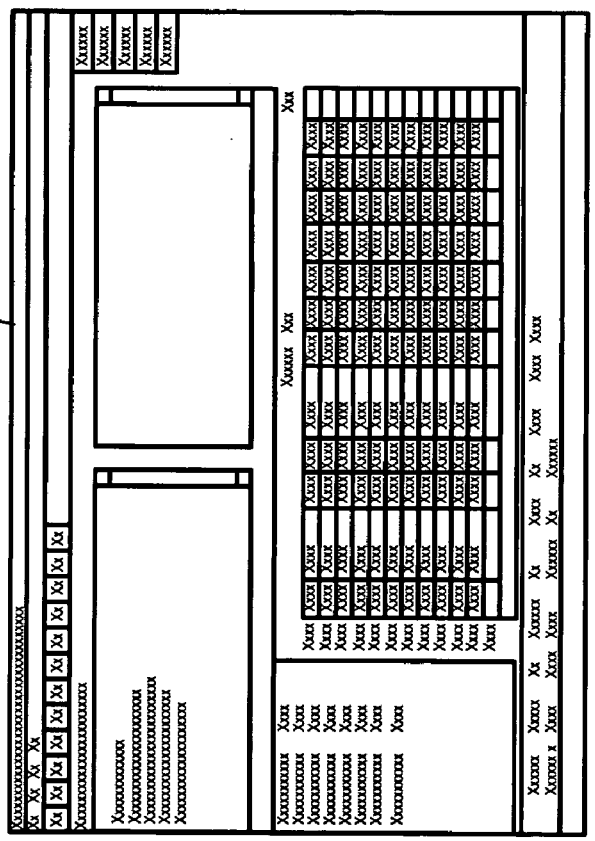
Figure 9:
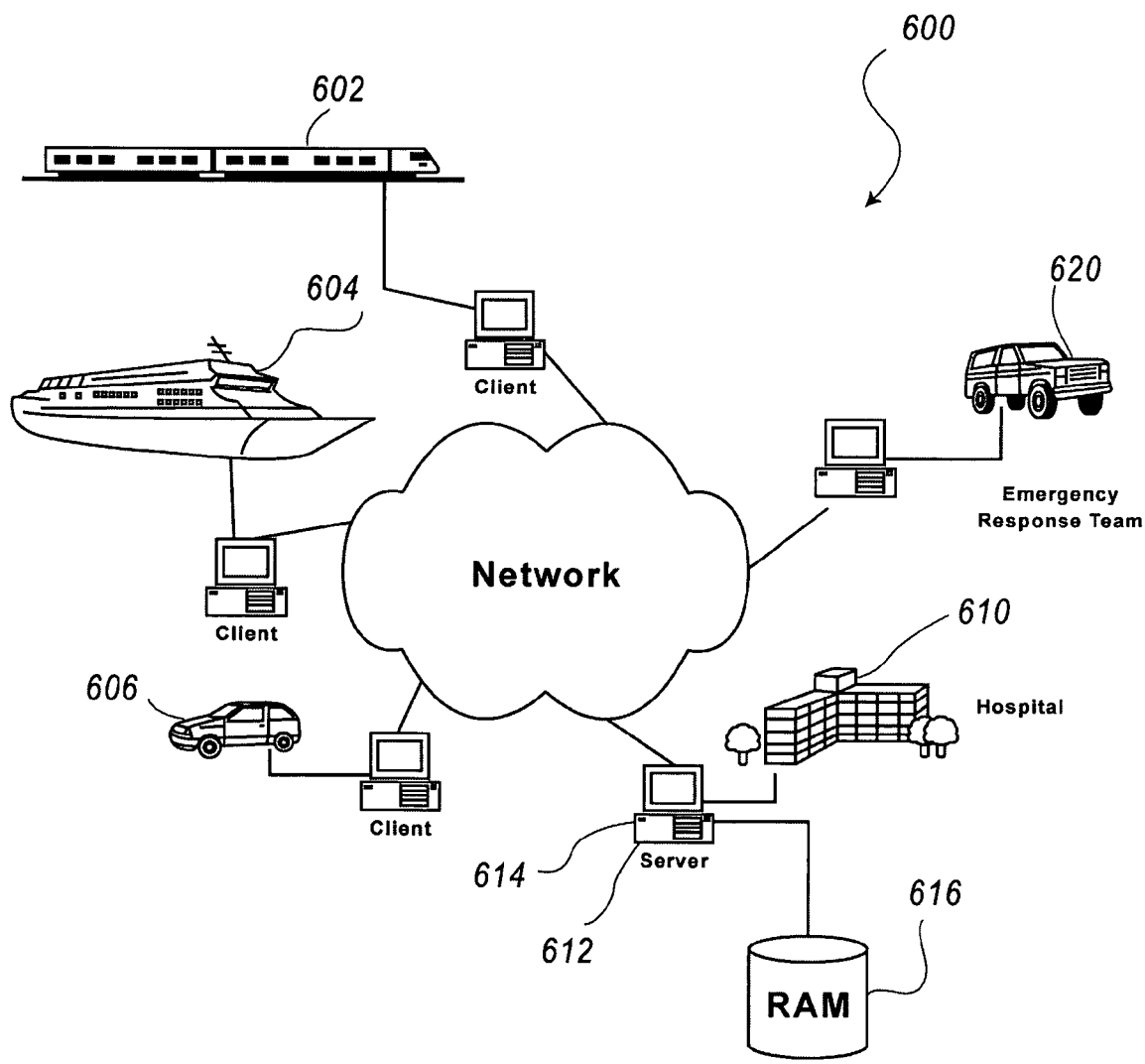
FIG. 9 shows a scheme of a tourniquet system treatment according to an exemplary embodiment of the present invention.
Figure 10:
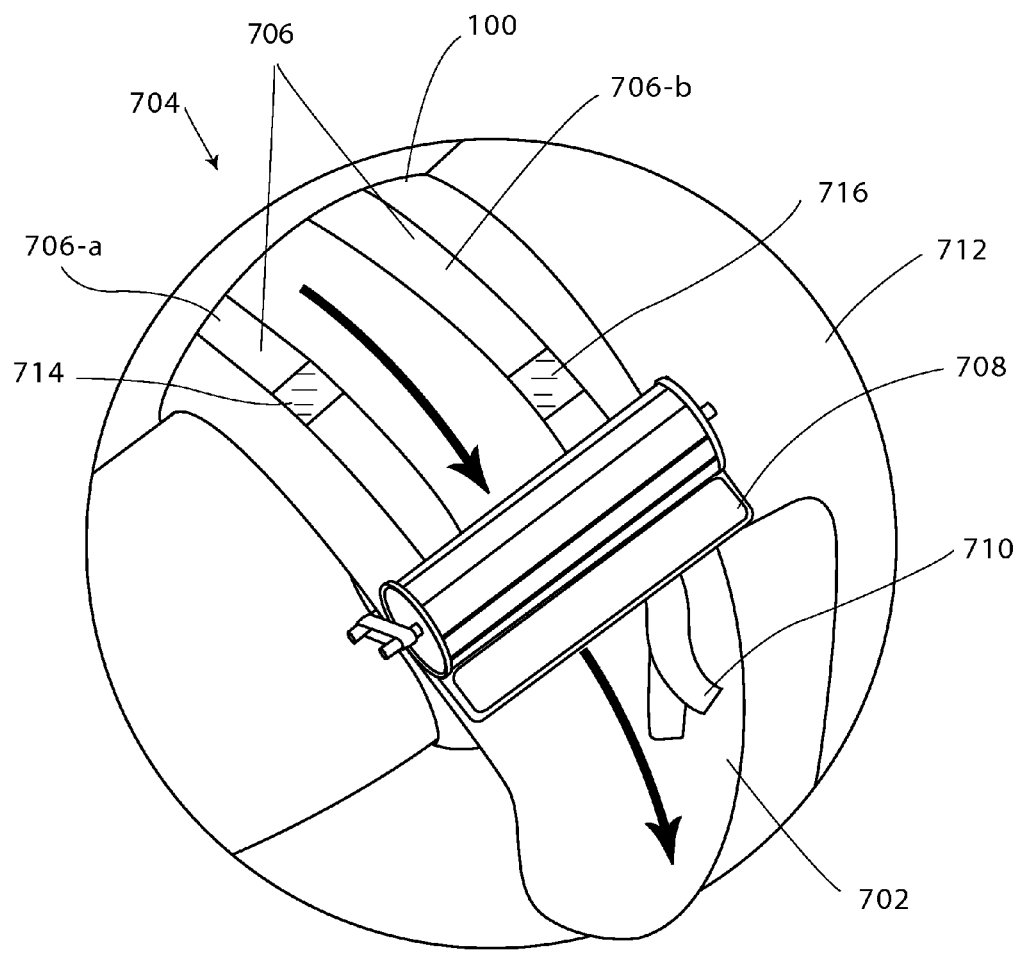
FIG. 10 shows a scheme of a tourniquet treatment system according to an exemplary embodiment of the present invention.

A schematic concept skeleton of tourniquet timer, in accordance with an exemplary embodiment of the invention, with various optional device components is shown in FIG. 1, a first exemplary implementation illustrating some features is shown in FIGS. 2-6, a second exemplary implementation is shown in FIGS. 7-9 and a third exemplary implementation is shown in FIG. 10. The Features shown for the apparatus according to the first, second and third implementations of the invention can be used together in one embodiment or independently from one another. In practical use, various types of tourniquets may be used together.

The present invention, in some embodiments thereof, provides a system for issuing an indication to a user whenever a tourniquet such as an arterial tourniquet and/or an exsanguination tourniquet (e.g., a rolling torus) has been applied for a certain time period surpassing a threshold. A tourniquet 100 (see FIG. 1) in accordance with some embodiments of the present invention consists of several components configured schematically as described further with reference to FIGS. 2-10.

Timer and Alert Mechanism

Figure 2:
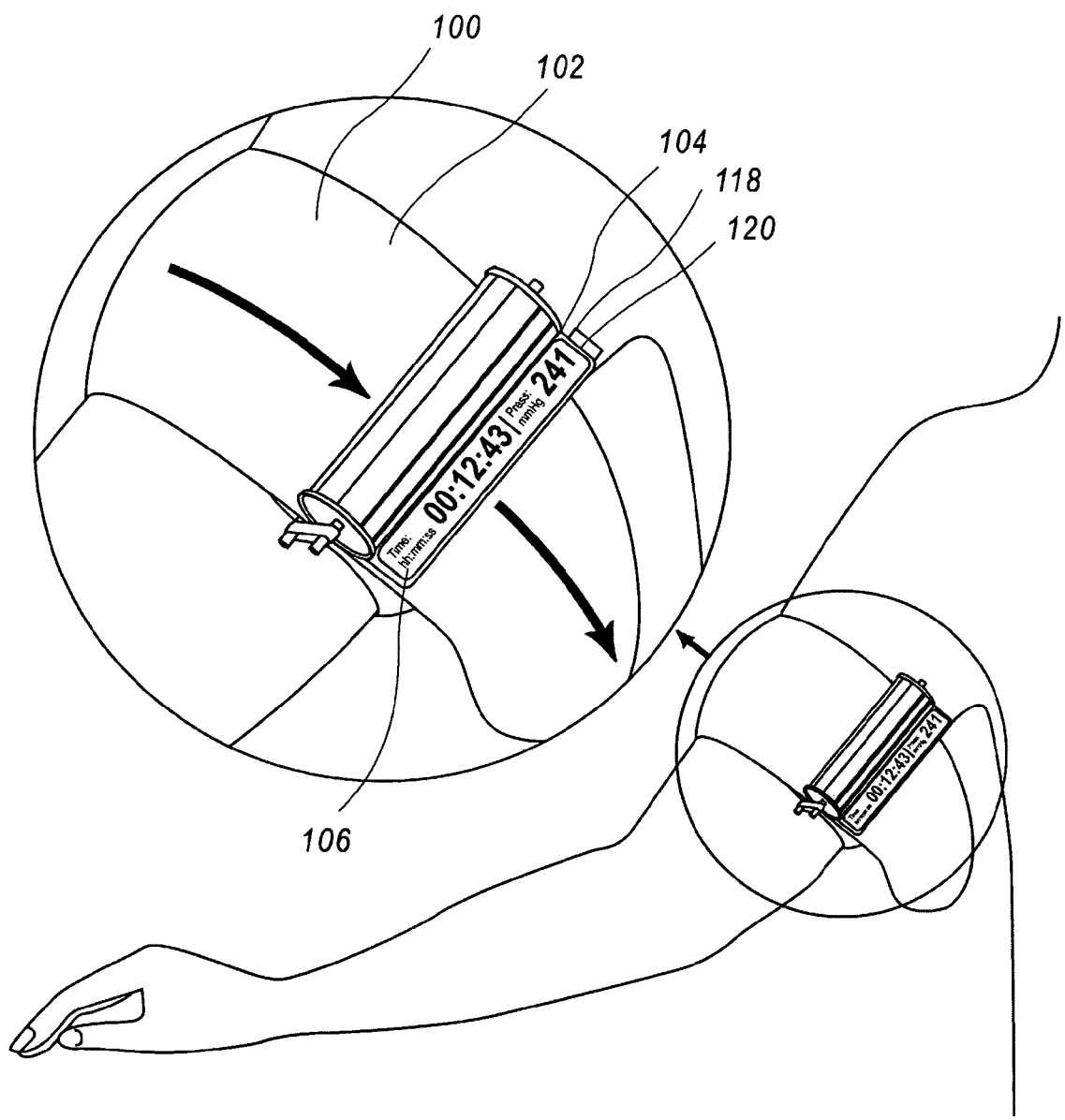
FIG. 2 shows a general view of the proposed apparatus according to a first embodiment of the present invention.
Figure 4:
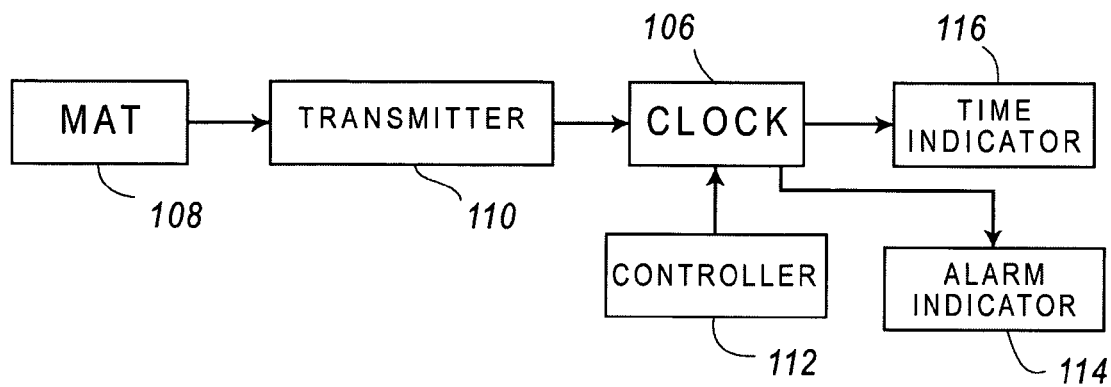
FIG. 4 shows a scheme of the tourniquet timer activation, in accordance with an exemplary embodiment of the invention.
Figure 3:
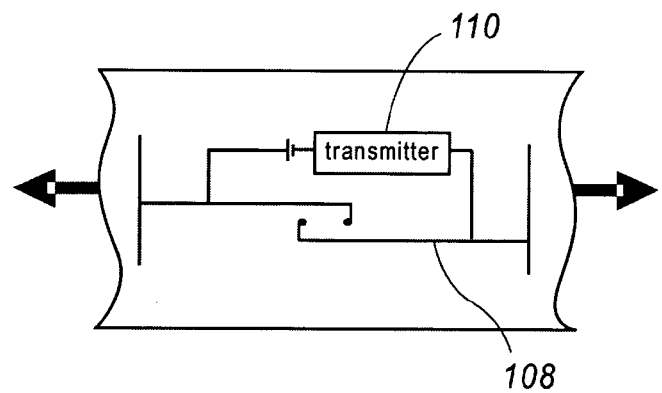
FIG. 3 shows a scheme of a pressure sensitive means with a transmitter, in accordance with an exemplary embodiment of the invention.

An exemplary tourniquet 100 according to a first embodiment of the present invention, see FIGS. 2-4 comprising pressure applying means 102 and timer 104 with an optional timer clock 106 (FIG. 2, 4). Pressure applying means 102 is mounted on a limb for surrounding it so as to block arterial flow therein.

In an exemplary embodiment of the invention, timer 104 is mechanically coupled to pressure applying means 102. In alternative embodiments, the timer is coupled to controller 112 which may be remote from pressure applying means 102. In some embodiments, timer 104 is aware of the exact time that pressure applying means 102 is activated. In other embodiments, timer 104 is aware only of an estimated time, which may be generated, for example, manually or automatically.

In an exemplary embodiment of the invention, the warning is generated by timer 104 when a danger time is reached and based on the estimated start time.

In other embodiments, the warning is generated by timer 104 twice, once before and once when a danger time is reached.

Optionally, the first warning is generated by timer 104 before a danger time is reached and realized in the time period from the moment of tourniquet 100 activation up to a danger time marked on this timer 104. This first warning is optionally based on preloaded or after provided patient's information, including data such as patient's age, instantaneous blood flow, blood pressure.

The second warning is optionally generated by timer 104 when a danger time is reached and based on the estimated start time. Optionally, a user input (not shown, such as a button) is provided to reset the time or to add a fixed amount of time before a next warning, for example, 5 minutes steps. Optionally, the number of thus added steps and/or time is counted and used in formulating the next alert, for example, the next alert indicating how often the timer had been updated and/or by how much and/or a total timer duration.

In an exemplary embodiment of the invention, pressure applying means 102 is supplied with a pressure-sensitive means (PSM)—trigger 108. PSM 102 is supplied also with transmitter 110 which transmits a signal responsive to at least one of the activation of timer 104 and activation of pressure applying means 102. The pressure applying means 102 and the pressure-sensitive means (PSM)—trigger 108 may be formed as a single means which is equipped with an independent energy source (not shown on the drawings, such as a battery).

The pressure-sensitive means (PSM) which is made optionally as mechanically activated trigger (MAT) 108, is activated by the usage of pressure applying means 102 and sends a signal through transmitter 110 (FIGS. 3, 4) to initialize timer clock 106 of timer 104. Then timer clock 106, configured electronically by controller 112, counts time (e.g., up or down) until a threshold previously entered (or pre-set) through controller 112 is reached. Alarm indicator 114 is activated when that threshold is surpassed by timer clock 106. Optionally, time indicator 116 shows the time after beginning initialization of timer clock 106. In some embodiments, other logics are used. In addition, non-fixed times may be provided for including times calculated based on patient condition and times inputted by a user when activating the tourniquet.

Optionally, timer 104 is supplied with rest button 118 and/or reset button 120 (FIG. 2) for its stop and reset operations.

Optionally, pressure source 122 (FIG. 1) serves for supplying pressure of tourniquet 100 attached around a limb such as to block blood flow therein.

Optionally, user input 124 serves for manually estimating a start time on timer 104 which usually is estimated automatically.

Optionally, timer 104 is supplied by pressure and time display 126 and physiologic interface 128 with a patient's data (FIG. 1). Alert means 130 serves for applying of the sound, light and other warning signals.

Mechanically Activated Trigger (MAT)

In some embodiments of the invention, trigger 108 is activated as a result of a certain mechanical stimulus it received. Such stimuli are, inter alia, mechanical stretching, tensile force, deformation bending and/or other change in mechanical property of the arterial tourniquet that can be used to activate the trigger. For example, when the tourniquet is applied to the limb and sufficient pressure (e.g., towards limb) or force (e.g., along tourniquet) has been applied, the trigger is activated.

Mechanically activated trigger (MAT) 108 (FIG. 3) may be made as a mechanical stretching sensor, a tensile force sensor or a deformation bending sensor. Every of these sensors may be made as an elastic or spring loaded micro-switch embedded within and/or mounted on the arterial or exsanguination tourniquet and is activated by stretching, for example as schematically shown in FIGS. 3, 4. Optionally, the tourniquet is formed of a stretchable matrix.

The tourniquet according to one embodiment of the present invention operates as follows (see FIGS. 1-6).

After tourniquet 100 attaching 400 (FIG. 5) around a limb so as to block blood flow therein, a start time for the attaching is estimated 402 on timer 104, for example, automatically 404 or manually 406 by user input 124. The time is optionally estimated for when tourniquet 100 is activated by start 408 of timer 104 and optionally used to automatically determine the application duration of tourniquet 100 to a limb. A correction for the estimation may be applied, for example, allowing for a few seconds between mounting the tourniquet and reaching operational pressure. Optionally, it is possible to rest 410 or reset 412 tourniquet's timer 104 by rest button 118 or reset button 120. When trigger 108 has been actuated, it sends a triggering signal to transmitter 110 which sends an initialization signal to timer clock 106 of timer 104. As noted above, some embodiments allow the time threshold (and/or passed time) to be changed. Optionally, a pressure is estimated using circuitry based on tension values.

The first warning 414 is generated by timer 104 before a danger time is reached and based on the patient's information 416 about the worsening of the patient's condition. The first warning 414 is realized in the time period from the moment of tourniquet 100 activation up to a danger time marked on timer 104. It is based on preloaded or after provided patient's information 416, including a date such as patient's age, instantaneous blood flow, blood pressure, etc.

The generating of the first warning 414 before a danger time is reached, sets in motion an optional automatic (or manual) the opening and then re-closing 418 of tourniquet 100 in response to this warning 414 and the data preloaded in timer 104. As noted above, the procedure may be changed to accommodate the time remaining.

The second warning 420 is generated by timer 104 when a danger time is reached which is based on the estimated start time. The generating of the second warning 420 when a danger time is reached optionally sets in motion tourniquet 100 deactivation 422.

In an exemplary embodiment of the invention, the generating of the first and/or the second warning 414 and 420 is accompanied with sound and/or light signals 424, an optional wireless transmitting detailed warning 426 may be of same complexity or more complex, for example causing the generation of speech, texts, including detailed warning with instructions for a user. Speech, text warnings may also be used for a non-wireless warning.

For example, the alarm indicator 114 shown in FIG. 1, 4 may indicate when a pre-set duration is elapsed by a visual or acoustic signal. Optionally, programming of sub-intervals for announcement, is provided. Once the pre-set maximum threshold duration, e.g. 2 hours, has been reached, the alarm is optionally activated in a persistent mode.

The tourniquet deactivation 422 ends 428 tourniquet 100 operations. FIG. 6 shows a graph of tourniquet control which is performed in 400-428 including stopping, opening and re-closing the tourniquet operations and showing an example where pressure is optionally increased over time, for example, as needed, rather than being maintained contrast. As shown, the rate of pressure application is optionally controlled and reduced optionally based on a measurement of actual change in pressure.

Wireless Control Configuration

According to some embodiments of the present invention shown in FIGS. 7-9, there is provided a tourniquet system 500 with wireless central control for one or more tourniquets 502, which may be of the type of tourniquets described above or not.

Optionally, tourniquet system 500 (FIG. 7) comprises a plurality of tourniquets 502 with pressure applying means 504 and transmitters 506 coupled with these means. Every transmitter 506 sends a signal associated with activation of the pressure applying means 504 and/or other functional changes, such as pressure measurements and/or a signal associated with an alarm.

Tourniquet system 500 optionally comprises a remote controller, e.g., computer 510 with a transceiver 512 (or at least a receiver) and circuitry display 514 to generate a signal detectable by a user regarding to the status of tourniquet 502 that sends a signal, based on the signal, associated with the usage of pressure applying means 504.

Alert signal 516, detectable by a user and displayed on the circuitry display 514, may include, for example, a tourniquet's ID-number, data of a patient, the time of tourniquet 502 attaching 400, the time of activation of pressure applying means 504, the time of generating of the first and the second warning 414 and 420 before and when a danger time is reached, the time of the user's input to the system, etc. (FIGS. 5, 8a, 8b). This signal may also include the information regarding to the status of at least one tourniquet 502 if it is applied to a limb or being in the reserve.

The signal detectable by a user is displayed on circuitry display 514 (FIGS. 5, 8a, 8b) (and/or a speaker and/or sent to a users portable communication device and/or electronic communicator, such as e-mail), when at least one tourniquet 502 sends by its transmitter 506 a signal associated with activation of pressure applying means 504. This signal detectable by a user is optionally changed on circuitry display 514, when at least one tourniquet 502 sends by its transmitter 506 the signals associated with the generating the first and/or the second warning signals 414 and/or 420 before and when a danger time is reached.

According to some embodiments of the invention, computer 510 with circuitry display 514, which is supplied with transceiver 512 and at least one timer 518 for monitoring at least one of multiple tourniquets 502, is mounted on remote station 520 (FIG. 7). These number of tourniquets 502 which are connected with the remote station 520 and computer 510 may be limited by the specific communication and processing and display abilities of computer 510, transceiver 512 and timer 518.

According to some embodiments of the invention, remote station 520 with computer 510, transceiver 512 and at least one timer 518 for monitoring the multiple tourniquets 502, may be made in a stationary design for the hospital use or in portable design to be used in military and emergency situations (FIGS. 7-9). Portability may be provided, for example, for an emergency vehicle. Optionally, when a tourniquet is moved from the area of one monitoring device (e.g., ambulance) to another (e.g., hospital), it detects the new device and registers with it. Such registration may include uploading of patient information and/or profile of use. Optionally or alternatively, registering includes downloading of instructions and/or data, such as patient information, to the tourniquet. Optionally, an alarm is sounded by the tourniquet if no monitor is found. Optionally, a monitor is looked for periodically, for example, every few minutes. Optionally, the tourniquet generates a time-based alarm if no monitor is found and/or even if one is found. The type of alarm may change based on the existence of a monitor. Alternatively or additionally, when a monitor is found, the monitor may be used for calculating a more precise danger time, for example, based on patient information.

According to another embodiment of the invention, remote station 520 with computer 510, transceiver 512 and at least one timer means 518, is within a mobile patient monitor or within an anesthesia monitoring system with possibility of communication to a pre-set cellular phone number via cellular phone 522 (FIG. 7).

According to some embodiments of the invention, remote station 520 with computer 510, transceiver 512 and at least one timer means 518, has feedback connections with each of multiple tourniquets 502 via one of wireless (or wired) connection modes, including, for example, satellite 524 modes (see FIG. 7), for initializing the stop or release operations of tourniquets 502, their opening and then re-closing or complete deactivation and/or for reporting.

Exemplary Signals Transmission

In an exemplary embodiment of the invention, the signal from trigger 108 is transmitted by transmitter 110 to timer 106. When wireless transmission is used, trigger 108 is optionally equipped with an energy source such as a micro-battery. The wireless signal can be transmitted as one of the following modes:

(i) Induction,
(ii) Magnetic field change,
(iii) Radio frequency transmission,
(iv) Bluetooth transmission,
(v) Other methods of wireless transmission known in the art.

Bluetooth Transmission

In an exemplary embodiment of the invention, Bluetooth transmission is used. The Bluetooth transceiver operates in the globally available 2.4 GHz ISM band. To achieve the short-range transceivers are integrated into devices either directly or through an adapter device such as a PC Card.

The Bluetooth core specification classifies the transmitter equipment as having three classes of radio transmission power, namely 100 mW (20 dBm), 2.5 mW (4 dBm) and 1 mW (0 dBm). With 0 dBm power, the communication range may be up to 10 meters (30 feet), while 20 dBm transmit power increases the range to 100 meters (328 feet). The baseband is responsible for channel coding and decoding the low level control of the timing and management of the link. Addressing and link control fields are added to the raw payload data and provide error detection and correction. The Bluetooth devices exist in either Slave or Master modes of operation and communicate between each other in miniature networks known as piconets.

Tourniquet system 500 according to an exemplary embodiment of the present invention operates as follows.

The detailed warning (if any) may be wireless transmitted to central computer 510 with one display 514 for performing the data from several tourniquets 502 (FIGS. 7-9). The invention may be realized, for example in case of emergency, on the base of several tourniquets 502 that is controlled by one timer 518 connected with central computer 510. Optionally, a less detailed warning is sent and the details are added by computer 510.

In another embodiment of this invention, remote station 520 with computer 510, transceiver 512 and at least one timer means 518 is within the anesthesia monitoring system with or without possibility of communication to a pre-set cellular phone number via an optional cellular phone 522.

Computer 510, transceiver 512 and at least one timer means 518 may be also in-part of a mobile patient's monitor (or other medical monitor or other device) with possibility of communication to a remote station 520. Tourniquets 502 according to these embodiments of the present invention operate in the same way as the tourniquets according to the first one.

Optionally, alarm 516 is automatically triggered (possibly with a different alarm indication, such as "check for inadvertent opening") when the arterial or exsanguination tourniquet 502 is released.

Optionally, alarm 516 is turned off by entering a specific identifying code of the person who inactivates the alarm. This information may be recorded by the central computer.

In an emergency, accidental or military situation, tourniquet system 500 which are on transport means 602, 604, 606 may determine the location of the nearest hospital 610 or medical emergency response team 620 (see FIG. 9) utilizing the Internet 600 or satellite mobile navigation system as an aid. Tourniquet system 500 may then contact hospital 610 server 612 (with computer system 614 and database 616) or medical emergency response team 604 via internet and/or satellite mobile communication system and notify the hospital or team of the patients with the tourniquets location (and optional application time) and requesting assistance. Depending on the type of tourniquet equipment on transport means 602, 604, 606, tourniquet system 500 may also transmit various vital characteristics of the patients (body temperature, pulse, blood pressure, etc). Optionally, a length of the tourniquet (e.g., based on an optical encoding of the band and a reader in a band locking element) is used to help identify the limb being treated Chemical Timer According to some embodiments of the invention, tourniquet 100 (see FIG. 10) uses a chemical timer means 704. Optionally, the chemical timer is used for one or both of identifying activation of the tourniquet and for showing an elapsed time of use. In some embodiments, no circuitry is provided at all and a visual warning is provide by the chemical timer In an exemplary embodiment of the invention, chemical timer 704 is coupled to pressure applying means 702 to do one or more of: at least estimate and/or note a start time of the application, to monitor a duration of this application and a patient's condition, to generate a first warning before a danger time is reached, based on the information about the worsening of the patient's condition and to generate a second warning when a danger time is reached, based on the estimated start time.

According to some embodiments of the invention, the chemical timer 704 comprises at least one strip 706 made of a material chosen from a group, including the liquid crystals, chemical compounds, leuco dyes, thermochromics, photochromics.

According to some embodiments of the invention, chemical timer 704 is made as at least one strip 706 of material which at least once changes its color under the affect of one or more agent chosen from a group, including light (package s light-proof), air (package may not include oxygen or may include an inhibiting gas), temperature (e.g., body temperature), tension (e.g., of strap), chemical activators (e.g., which are broken intentionally or inadvertently when tourniquet is used). Optionally, the chemical time becomes opaque in the form of a warning or transparent to show an underlying warning.

According to some embodiments of the invention, chemical timer 704 is activated by the input of the user who at least estimates a start time for attached tourniquet 100, makes the note of time when tourniquet 100 is activated and estimates the application duration of tourniquet 100 to a limb 712.

According to some embodiments of the invention, chemical timer 704 is activated by manual input of the user who turns therefore at least one handle 708 and/or tears off at least one strip 706 cover sheet 710 (FIG. 10).

Optionally, one strip 706-a of chemical timer 704 may generate a first warning (e.g., visual, or its color read by a sensor with a circuit that generates an alert) before a danger time is reached, based on the information about the worsening of the patient's condition, such as patient's blood pressure, instantaneous blood flow (FIG. 10). Other strip 706-b of chemical timer 704 may generate a second warning when a danger time is reached, based on the estimated start time. In an exemplary embodiment of the invention, multiple strips are provided, one for each of a different time duration, for example, 30 minutes, 50 minutes, 80 minutes and 120 minutes (e.g., if 2 hours is a maximum allowed time)

Optionally, the both strips 706-a and 706-b of chemical timer 704 together generate a first warning before a danger time is reached and a second warning when a danger time is reached.

In an exemplary embodiment of the invention, the tourniquet is operated as follows (see FIG. 10).

After tourniquet 100 attaching 400 (FIG. 10, 1, 5) around a limb so as to block blood flow therein, a start time for the attaching is estimated 402 on timer 704 manually 406 by the user input 124. Therefore, the user turns at least one handle 708 and/or tears off at least one strip 706 cover sheet 710 (FIG. 10).

Optionally, strip 706-a of chemical timer 704 generates a first warning by color section 714 (FIG. 10) before a danger time is reached. Optionally, different strips are provided for using in different patient conditions and/or procedures, optionally all provided on a same tourniquet. Other strip 706-b of chemical timer 704 generates a second warning by color section 716 (FIG. 10) when a danger time is reached, based on the estimated start time.

Optionally, the both strips 706-a and 706-b of chemical timer 704 may generate a first warning before a danger time is reached and a second warning when a danger time is reached.

Optionally, if strips 706-a and 706-b are made of the liquid crystals, they may be supplied by the trigger or the transceiver and equipped with an independent energy source (not shown in the drawings) and the detailed warning may be transmitted wirelessly to central computer such as described above In an exemplary embodiment of the invention, the tourniquets and/or timers 104, 518 and 704 are adapted to the sterilization by one of the methods from the group, including: gas, steam, ultraviolet or radiation sterilization. IPA the timer includes a sealed housing and/or is resistant to heat.

In an exemplary embodiment of the invention, a kit comprising a tourniquet and an integral timer are provided, optionally with instructions, in a sterile package.

In an exemplary embodiment of the invention, the timer is provided as a separate element and is adhesive or clip on or otherwise attachable to the tourniquet or other useful location (such as patient chest or forehead). For example, a chemical timer may be and adhesive strip which is optionally detached from tourniquet and placed on patient forehead.

Optionally, the chemical timer and/or other timers continue counting time even after the danger time is reached, for example, an extra hour or two. Separate chemical strips may be provided for this use.

Optionally, the mechanical trigger and/or chemical trigger operates at a same time as a battery. For example, when tensioned, the tourniquet allows the batter to contact atmospheric oxygen (for a zinc-air battery) or removes an isolator from a contact (for a different battery type). Optionally, the opening of the package of the tourniquet activates the battery and/or timer and/or estimates an activation time, for example, by tearing a circuit.

In an exemplary embodiment of the invention, an initiation signal is sent repeatedly several times (e.g., 20 times over a time of 15 minutes) to ensure it is properly sent and/or received.

In an exemplary embodiment of the invention, the alert signal is sent using a communication protocol with receiving confirmation and/or is sent multiple times, to ensure repeat. Failure to receive confirmation may cause a local alert. Failure to receive a signal from a remote tourniquet for a period of time may case an alert at the central computer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term is broader than, but includes, the terms "consisting essentially of" and "consisting of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions. Optionally, the methods described herein are used to program a general purpose computer and/or on a computer readable medium, such as an optical disk or a magnetic disk and/or stored a computer volatile and/or non-volatile memory and/or accessible over a network.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of using a tourniquet comprising: a) attaching a tourniquet around a limb so as to block blood flow therein, said tourniquet comprising: a) a pressure applicator adapted to be mounted on a limb so as to block arterial flow therein, wherein said pressure applicator is a mechanically activated trigger (MAT) comprising a tensile force sensitive element and a switch, wherein said switch is opened or closed based on said tensile force sensitive element, and a transmitter which transmits a signal responsive to activation of said pressure applicator in response to closure of said switch; and b) a timer configured to generate two warnings at two different times, including before a tourniquet danger time is reached, wherein said timer is initiated by said signal transmitted by said transmitter in response to closure of said switch; b) at least determining a start time for said attaching according to transmission of said signal from said transmitter; c) automatically generating a first warning before a danger time is reached as calculated by said timer; and d) automatically generating a second warning when a danger time is reached as calculated by said timer, based on said start time.

2. A method according to claim 1, wherein said first warning is generated based on an estimation of a patient condition.

3. A method of claim 2, wherein generating comprises using current patient information patient information.

4. A method of claim 3, wherein the patient information, includes one or more of patient age, instantaneous blood flow and blood pressure.

5. A method of claim 1, wherein estimating a start time for said attached tourniquet, comprises automatically detecting a signal indicating a tourniquet activation on a limb.

6. A method of claim 5, wherein said estimating comprises receiving a user input.

7. A method of claim 1, comprising opening and then re-closing tourniquet in response to the first warning.

8. A method of claim 1, comprising deactivating the tourniquet in response to the second warning.

9. A method of claim 1, wherein generating the first and the second warning comprises one or more of an audio, a visual and a speech alert.

10. A method of claim 9, wherein generating comprises transmitting a wireless signal to remotely generate an alert.

11. A method of claim 1, comprising simultaneously monitoring a plurality of warning signals from a plurality of tourniquets using a central controller.

12. A tourniquet, comprising: a) a pressure applicator adapted to be mounted on a limb so as to block arterial flow therein, wherein said pressure applicator is a mechanically activated trigger (MAT) comprising a tensile force sensitive element and a switch, wherein said switch is opened or closed based on said tensile force sensitive element, and a transmitter which transmits a signal responsive to activation of said pressure applicator in response to closure of said switch; and b) a timer configured to generate two warnings at two different times, including before a tourniquet danger time is reached, wherein said timer is initiated by said signal transmitted by said transmitter in response to closure of said switch.

13. The tourniquet of claim 12, comprising an alert generator.

14. The tourniquet of claim 12, wherein said timer is integral to said tourniquet.

15. The tourniquet of claim 12, wherein said timer is separate from said tourniquet.

16. The tourniquet of claim 12, comprising a packaging configured to start said timer when opened.

17. A tourniquet according to claim 12, wherein said timer is sterilizable.

18. The tourniquet of claim 12, wherein said timer further comprises circuitry configured to calculate a danger time of said tourniquet based on a condition of a patient.

19. A tourniquet system with wireless central monitoring for one or more tourniquets, comprising: (i) at least one tourniquet comprising: a) a pressure applicator adapted to be mounted on a limb so as to block arterial flow therein, wherein said pressure applicator is a mechanically activated trigger (MAT) comprising a tensile force sensitive element and a switch, wherein said switch is opened or closed based on said tensile force sensitive element, and a wireless transmitter which transmits a signal responsive to activation of said pressure applicator in response to closure of said switch; and b) a timer configured to generate two warnings at two different times, including before a tourniquet danger time is reached, wherein said timer is initiated by said signal transmitted by said transmitter in response to closure of said switch; and (ii) a remote controller with a receiver configured to receive said signal from said transmitter and a display configured to display a signal detectable by a user, responsive to said signal.

20. A system of claim 19, wherein said detectable signal comprises a warning of an elapsing of a time for using said tourniquet.

21. A system of claim 19, comprising a controller configured to release said tourniquet.

22. A system of claim 19, comprising circuitry configured to calculate a danger time of said tourniquet based on a condition of a patient.

23. A system of claim 19, wherein said remote controller is portable.

24. A system of claim 19, wherein said remote controller is configured for manually receiving information regarding an activation of at least one tourniquet.

25. A system of claim 19, comprising circuitry for registering a plurality of tourniquets.

26. A tourniquet, comprising: a) a pressure applicator adapted to be mounted on a limb so as to block arterial flow therein, wherein said pressure applicator is a mechanically activated trigger (MAT) comprising a mechanical stretching sensitive element or a deformation bending sensitive element, a switch, wherein said switch is opened or closed based on said mechanical stretching sensitive element or said deformation bending sensitive element, and a transmitter which transmits a signal responsive to activation of said pressure applicator in response to closure of said switch; and b) a timer configured to generate two warnings at two different times, including before a tourniquet danger time is reached, wherein said timer is initiated by said signal transmitted by said transmitter in response to closure of said switch.

* * * * *